United States Patent [19]

Gysi

[11] Patent Number: 5,703,300
[45] Date of Patent: Dec. 30, 1997

[54] CONTAINER INSPECTION APPARATUS

[75] Inventor: Peter Gysi, Bellikon, Switzerland

[73] Assignee: Elpatronic AG, Zug, Switzerland

[21] Appl. No.: 643,415

[22] Filed: May 9, 1996

[30] Foreign Application Priority Data

Jun. 8, 1995 [CH] Switzerland ............ 01-679/95-0

[51] Int. Cl.[6] ............................................. G01N 1/14
[52] U.S. Cl. ................ 73/863.91; 73/865.8; 73/863.81
[58] Field of Search ........................ 73/865.8, 865.9, 73/863.81, 863.85, 863.91, 863.92

[56] References Cited

U.S. PATENT DOCUMENTS

| | | |
|---|---|---|
| 3,266,292 | 8/1966 | Bailey. |
| 5,350,565 | 9/1994 | Leveson et al. ............... 422/64 |
| 5,376,550 | 12/1994 | Fine et al. ........................ 436/47 |
| 5,571,978 | 11/1996 | Gysi et al. ...................... 73/865.8 |

FOREIGN PATENT DOCUMENTS

| | | |
|---|---|---|
| A 0534096 | 3/1992 | European Pat. Off.. |
| A 0579952 | 1/1994 | European Pat. Off.. |
| U 9114357 | 5/1992 | Germany. |
| A 42 28 984 | 2/1994 | Germany. |

*Primary Examiner*—Thomas P. Noland
*Attorney, Agent, or Firm*—McCormick, Paulding & Huber

[57] ABSTRACT

A disk-like sampling head is arranged above a linear section of a conveyor path with a continuous flow of bottles. The sampling head is rotatable about an axis oriented transverse to the conveyor path, and preferably the axis is a horizontally-oriented axis. Rotation of the sampling head is synchronized with the continuous flow of bottles. The apparatus is particularly simple and inexpensive.

17 Claims, 8 Drawing Sheets

CONTAINER INSPECTION APPARATUS

BACKGROUND OF THE INVENTION

The invention relates to an apparatus for inspecting containers, in particular multi-trip bottles, for the presence of contamination, comprising a conveyor device for the containers and at least one sampling head extracting a sample from each individual container.

Known apparatus with a high bottle throughput uses a carousel conveyor, such as e.g. the apparatus according to EP-A 0579952, DE-U 9114357 or EP-A 0534096. Such a conveyor has the disadvantage of being relatively complex and expensive. Furthermore, such apparatus needs a lot of room. U.S. Pat. No. 3,266,292, on the other hand, discloses an inspection apparatus with a linear conveyor path. In this case, however, each container is halted so that the sampling head can be inserted, which makes apparatus of this type unsuitable for modern industrial inspection of containers, involving inspection of e.g. up to 1000 containers per minute, since the apparatus is incapable of attaining the required throughput of containers.

SUMMARY OF THE INVENTION

The object which lies at the basis of the invention is to provide an inspection apparatus which, with a simple, low-cost construction, is capable of achieving a high container throughput per unit of time, and which does not possess the disadvantages which have been mentioned.

This object can be realised in an inspection apparatus of the abovementioned kind by providing, in the inspection zone, a linear conveyor path for transporting containers continuously, above which a wheel-like or disk like sampling head is provided, parallel with the conveyor path and rotatable about an axis transverse to the conveyor path.

The provision of a linear conveyor path with continuous transport makes it possible to achieve a high throughput of containers with a simple, low-cost construction. The wheel-shaped or disk-shaped sampling head can be arranged above the conveyor path and parallel therewith to allow samples to be removed while straight-line transport of the containers is maintained without interruption, likewise permitting a high throughput of containers per unit of time. Moreover, when the gas samples are removed, the gas paths can be much shorter than in the known carousel apparatus.

BRIEF DESCRIPTION OF THE DRAWINGS

Embodiments of the invention will now be described in more detail by way of example, with reference to the accompanying drawings, in which.

DESCRIPTION OF THE PREFERRED EMBODIMENTS

Figure 1:
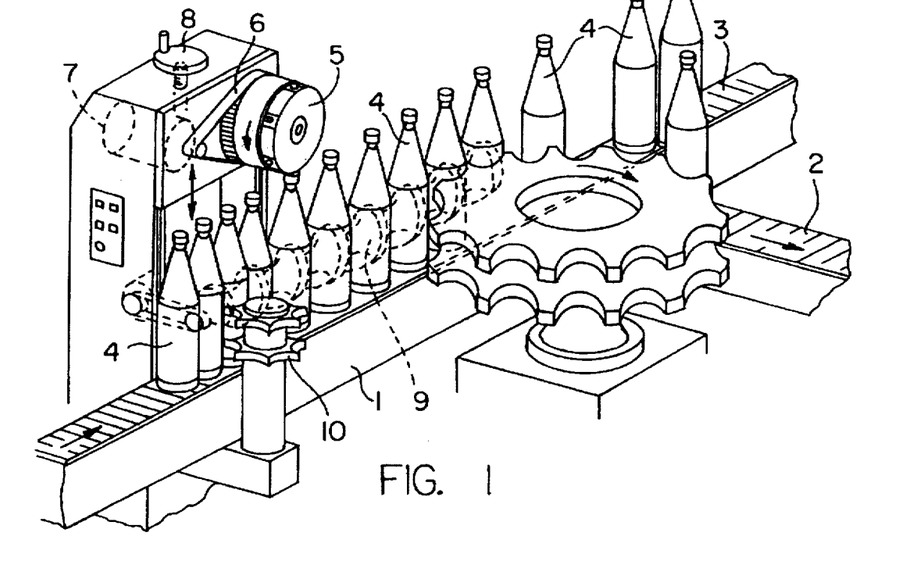
FIG. 1 is a schematic view of an apparatus according to the invention.

FIG. 1 shows schematically an apparatus according to the invention with a linear section 1 of a conveyor path and branching conveyor paths 2,3 leading therefrom downstream of the apparatus. A vertically arranged sampling head 5, which is rotatably driven—in the illustrated example, by a motor 7 through a toothed belt 6 —, is located above the containers 4 which are being continuously conveyed along the conveyor path 1. The height of the sampling head 5 above the conveyor path 1 is adjustable—as symbolised in FIG. 1 by the crank 8—to adapt the vertical position of the head 5 to the height of the containers. Along the linear section 1 of the conveyor path, the containers 4 are preferably positioned in a precise and positive fashion, e.g. by means of the worm 9 drawn in broken lines. A star wheel 10 may be provided at the start of the straight section 1 to control the entry of containers 4 into the screw 9 whilst also acting as an excluder. The precise positioning of the containers 4 ensures that the motion of the containers and that of the sampling head 5 are positively synchronised. A diverter module with branching conveyor paths 2,3 may be provided to divert those containers which are identified upon inspection as defective, so that e.g. bottles identified as sound are guided into conveyor path 2, and bottles identified as unsound into conveyor path 3. Other known selection options may of course be used, e.g. ejectors or switch points.

Figure 1A:
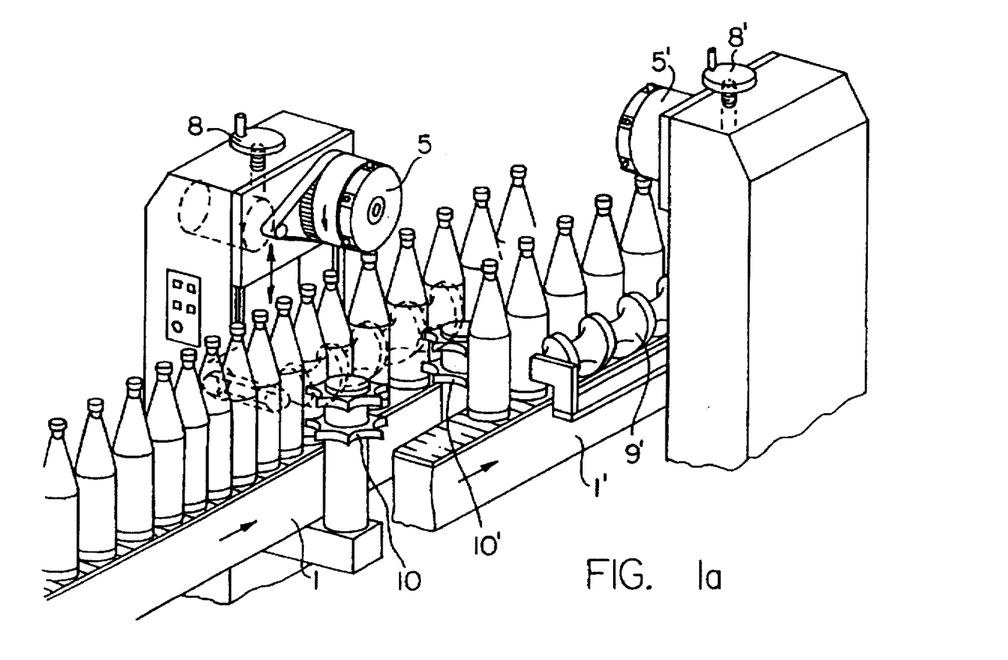
FIG. 1a is a schematic view showing the arrangement of two sets of the apparatus shown in FIG. 1.

The simple construction of the apparatus shown enables it to be installed without any problem alongside a conveyor line. Two or more sets of such apparatus may also be arranged in series. On parallel conveyor lines, two sets of apparatus can easily be deployed, as seen in FIG. 1a.

Figure 2:
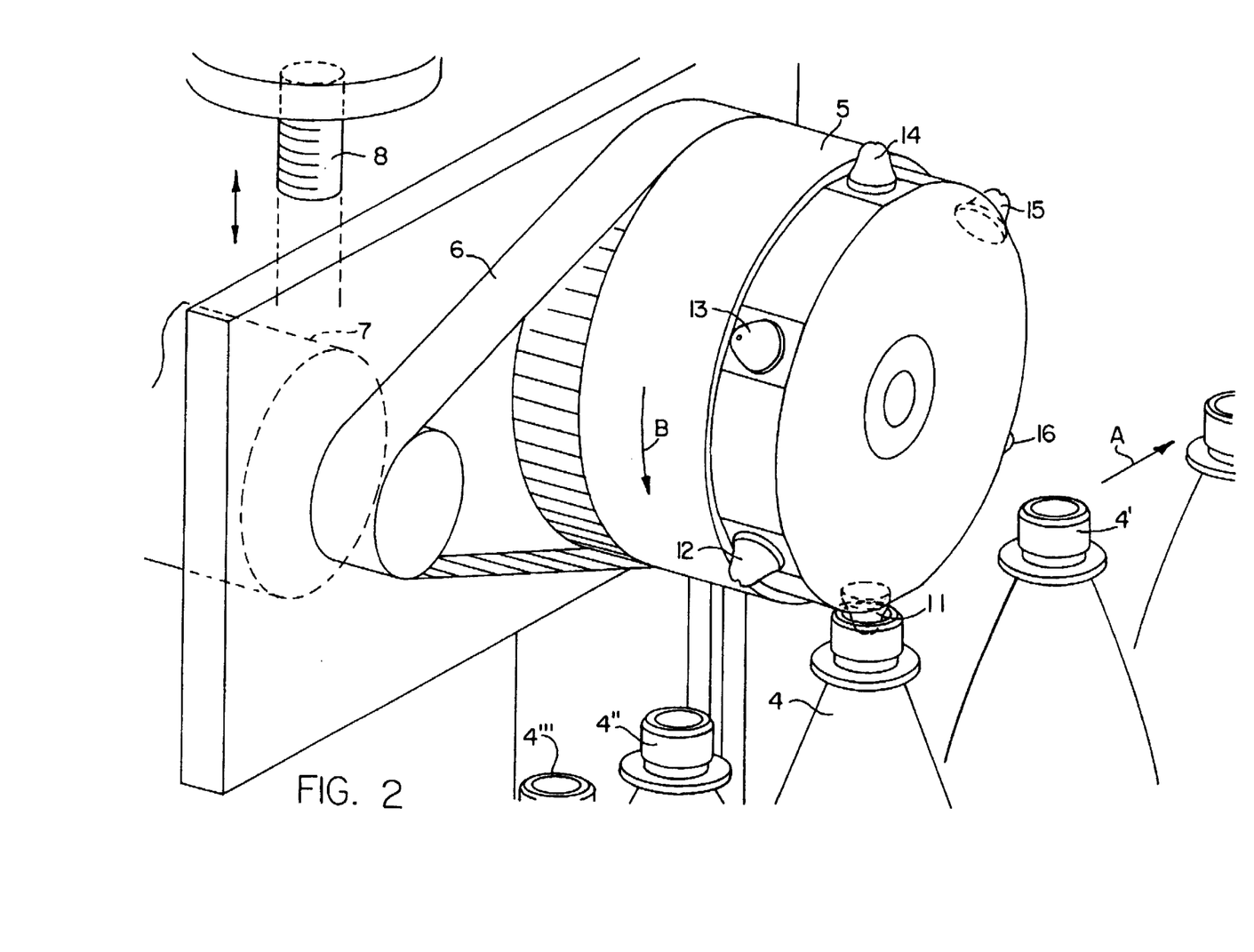
FIG. 2 is a schematic view of the sampling head above the straight conveyor path with the containers.

FIG. 2 is a highly schematic view of the driven sampling head 5, showing how it dips into the individual containers. In the example shown, the sampling head 5 is disk-shaped and is equipped with six projecting sampling elements 11 to 16 on its circumference. As the sampling head 5 rotates, the projecting elements 11 to 16 dip in succession into the passing train of containers 4, without contacting them. Thus, in the illustrated position, the element 11 is dipping into the container 4, while the element 16 has vacated the container 4'. As the containers are conveyed in a straight line in the direction of the arrow A and the head 5 rotates in the direction of the arrow B (these motions being synchronised with each other), the element 12 then dips into the container 4" as the element 11 leaves the container 4 once more. The element 13 then dips into the container 4''', and so on.

Figure 3:
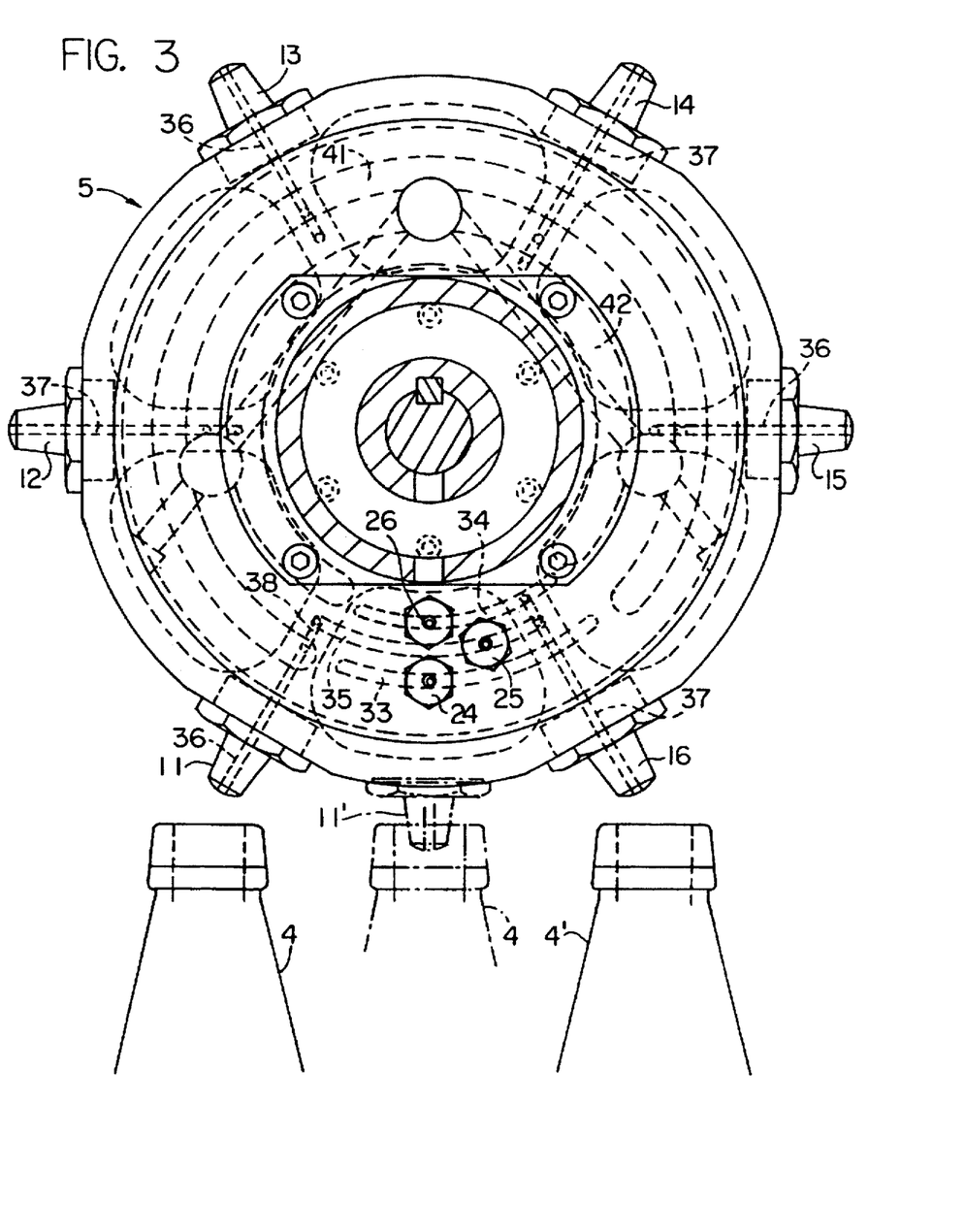
FIG. 3 is a front view of a sampling head.
Figures 4, 4A:
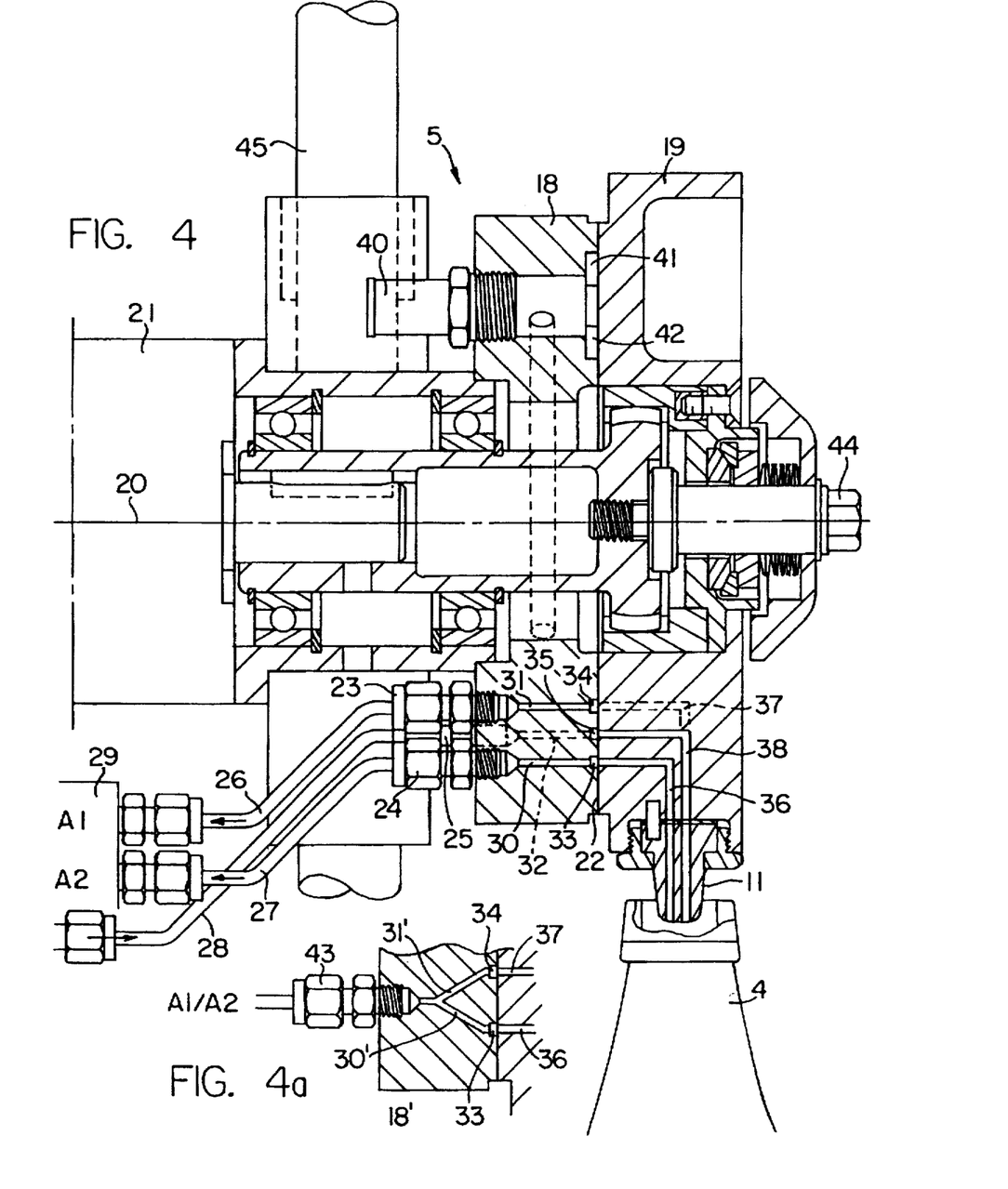
FIG. 4 is a vertical section through the sampling head of FIG. 3.
FIG. 4a shows an alternative configuration of the sample gas passageways in the embodiment of FIG. 4.

FIGS. 3 and 4 show in greater detail the construction of a sampling head for the removal of gas samples. The sampling head 5 is shown in FIG. 3 in a front view, with passageways located within the head indicated in broken lines, and with an intermediate position of one of the projecting elements likewise shown in broken lines. FIG. 4 is a vertical section. The sampling head 5 in the illustrated example also serves as a distributor head for the gas samples. A distributor head is already known in principle from EP-A 579952.

In the example shown, the sampling head has a fixed part 18 and a rotating part 19 which can be rotated about a central axis 20 by a motor 21. The rotational speed of the motor is synchronised with the speed of the conveyor. The fixed part 18 and the rotating part 19 are in contact over sliding and sealing faces 22. Connections 23 and 24 are provided on the fixed part 18 to carry away the gas samples removed from the containers. The samples are drawn via lines 26 and 27 into two analysing instruments A1,A2, which are simply shown lumped together as one block 29, and will not be described further here, as such instruments are known. Preferably these analysing instruments are mass spectrometers or detectors of polycyclic aromatic hydrocarbons. The fixed part 18 is also provided with a connection 25 for a compressed air line 28 whereby—in a known manner—air can be blown into the container as the gas sample is being removed. Corresponding ducts 30,31,32 for the gas samples and for compressed air lead to arc-shaped chambers 33,34 and 35 within the fixed part 18. The chambers 33,32,35 are in communication with corresponding ducts 36,37 and 38 in the rotating part 19 when the ducts are brought into register with the chambers by the movement of the rotating part 19. Ducts 36 and 38 lead through the projecting elements 11,13 and 15, where they open to atmosphere. Ducts 37 and 38 lead through the projecting elements 12,14 and 16, where they open to atmosphere. Depending on the application, these projecting elements, or "mouth pieces", may be made of metal, plastic, or an elastomer, and may be shaped to suit the specific container mouth, so that they never come into contact with the container mouth, thus avoiding contamination. In the present example they are fixed, easily replaceable parts, each provided with an anti-rotation locking pin.

The fixed part 18 is also provided with a connection 40 for a suction pump (not shown). The connection 40 is in communication with two chambers 41 and 42 each in the form of a segment of a circular ring. The projecting elements 11 to 16, that is to say the ducts 36 and 37 provided in these elements, are in communication with the chambers 41 and 42 as they rotate, except during the time when communication is established with the chambers 33 and 34 and the gas sample is being removed from the container, so that, as the projecting elements 11 to 16 rotate, atmospheric air is sucked in through them, and passes via the chambers 41 and 42 and the connection 40 to the suction pump. This intake of atmospheric air serves to purge the projecting elements 11 to 16 i.e. the ducts therein.

The mode of operation for feeding gas samples alternately to the analysing instruments A1 and A2 in the block 29 may be described as follows. The projecting element 11 is in the position drawn in unbroken lines in FIG. 3 shortly before dipping into the container 4 (which is likewise drawn in unbroken lines). The passageway 36 in the element 11 is still in communication with the air intake passage 41, and air drawn in above the container mouth is being conveyed to the suction pump via the suction pump connection 40. In this position of the element 11, the passageway 38 has just come into register with the compressed air passage 35, so that compressed air which is being supplied from the compressed air source via the line 28 escapes from the element 11. Thus injection of compressed air into the container 4 is already beginning, resulting in more intensive mixing of the air in the container with foreign substances to be analysed. It is also possible to provide a device upstream of the sampling head to introduce a medium, such as compressed air, into the containers.

As the head 5, and with it the element 11, continues to rotate, and as the container 4 continues to be conveyed along its path, the element 11 dips into the container 4. As this is happening, the passageway 36 in the element 11 comes out of register with the intake chamber 41, but into register with the intake chamber 33 and its associated duct 30, and hence into communication via the line 27 with the analysing instrument A2, which is thus able to draw a gas sample from the container for analysis. The duct 38 in the element 11 remains in communication with the compressed air chamber 35. FIG. 3 illustrates in broken lines a position of the element 11, and of the container 4, which corresponds to maximum insertion of the element 11 into the container 4.

The element 16 in FIG. 3 has already emerged from the dipping phase and has vacated the corresponding container 4'. The passageway 37 in the element 16 is still in communication, via the chamber 34 and the passageway 31 and line 26, with the analysing instrument A1 (i.e. not the same analysing instrument as the element 11). Also, compressed air is still being discharged via the passageway 38 in the element 16 and the passageway 32 and line 28. However, as the head 5 rotates a little further, the passageway 37 in the element 16 comes into register with the air intake passage 42, ending the supply of gas drawn from the container 4', through the element 16, to the analysing instrument A1.

The projecting element 12 becomes the next element to dip into a container (the next and subsequent containers are not shown in the drawing). In turn this element 12 has a passageway 37 (like the element 16), and therefore after it comes out of register with the air intake passage 42 comes into register with the gas sample intake passage 34 and hence into communication with the analysing instrument A1. The next element 13, on the other hand, has a passageway 36 (like the element 11), and consequently comes into communication with the analysing instrument A2 via the chamber 33, passageway 30, and line 27. In this way, successive elements 11 to 16 dipping into the train of containers are positively assigned to one or other of the analysing instruments A1 and A2, and gas samples from successive containers are despatched alternately to the analysing instruments FIG. 1a shows an alternative configuration of the passageways 30 and 31 as passageways 30' and 31' leading to a single analysing instrument connection 43. This permits operation with a single analysing instrument, say the instrument A1 for example, when instrument A2 has to be serviced or repaired, or in any circumstances in which only a single analysing instrument is required. The changeover to a single analysing instrument can be made relatively easily by replacing the fixed part 18 (FIG. 4) with the part 18' (FIG. 4a). The replacement can be made quickly, as the head 5 is easily accessible (unlike the known carousel arrangement), and can be quickly removed and refitted after undoing the central fastener In the illustrated example the height is adjusted e.g. by means of a spindle 45 which sets the vertical position of the head 5 together with its drive motor 21.

Figure 5:
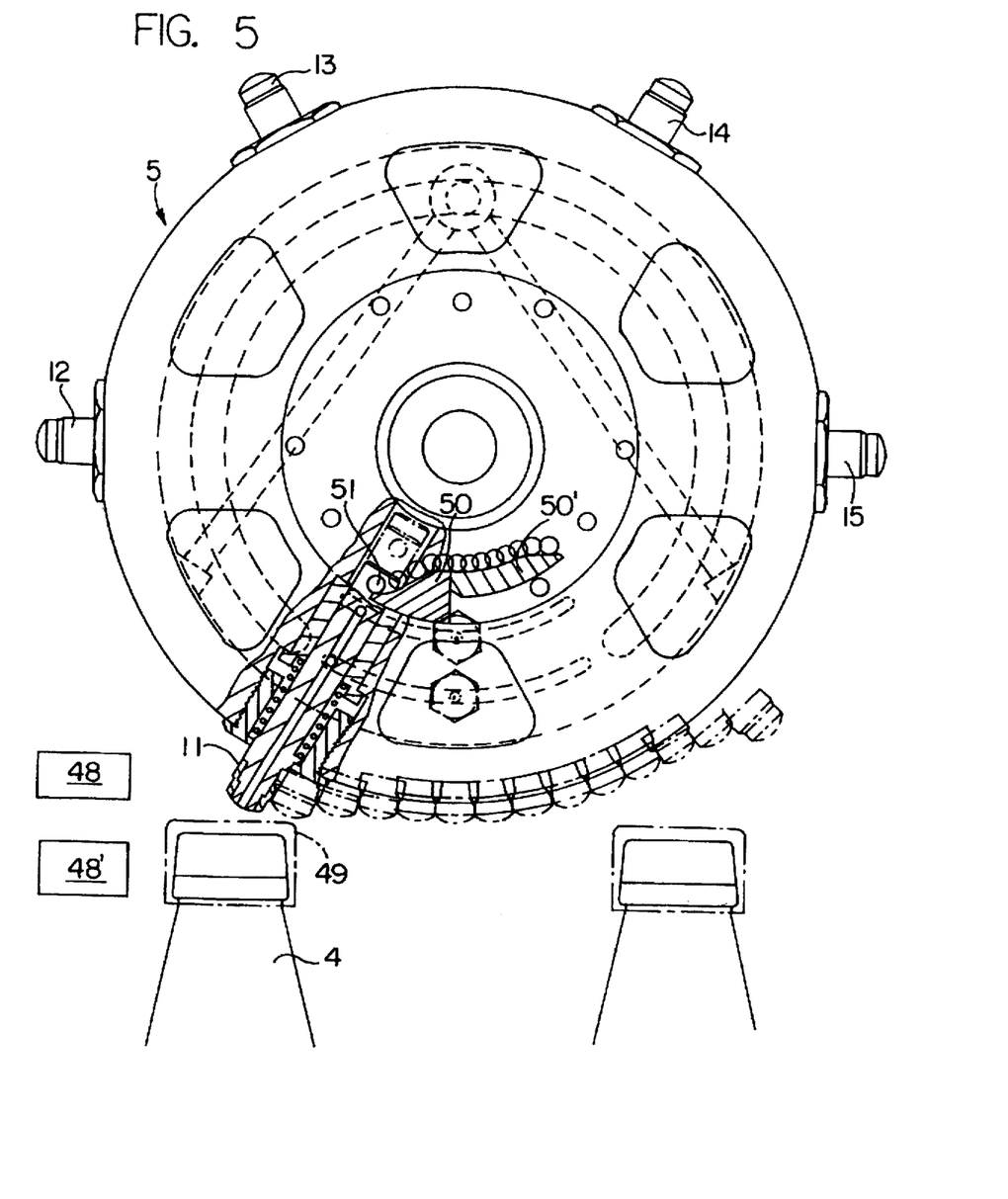
FIG. 5 is a front view of another sampling head.
Figures 6, 7:
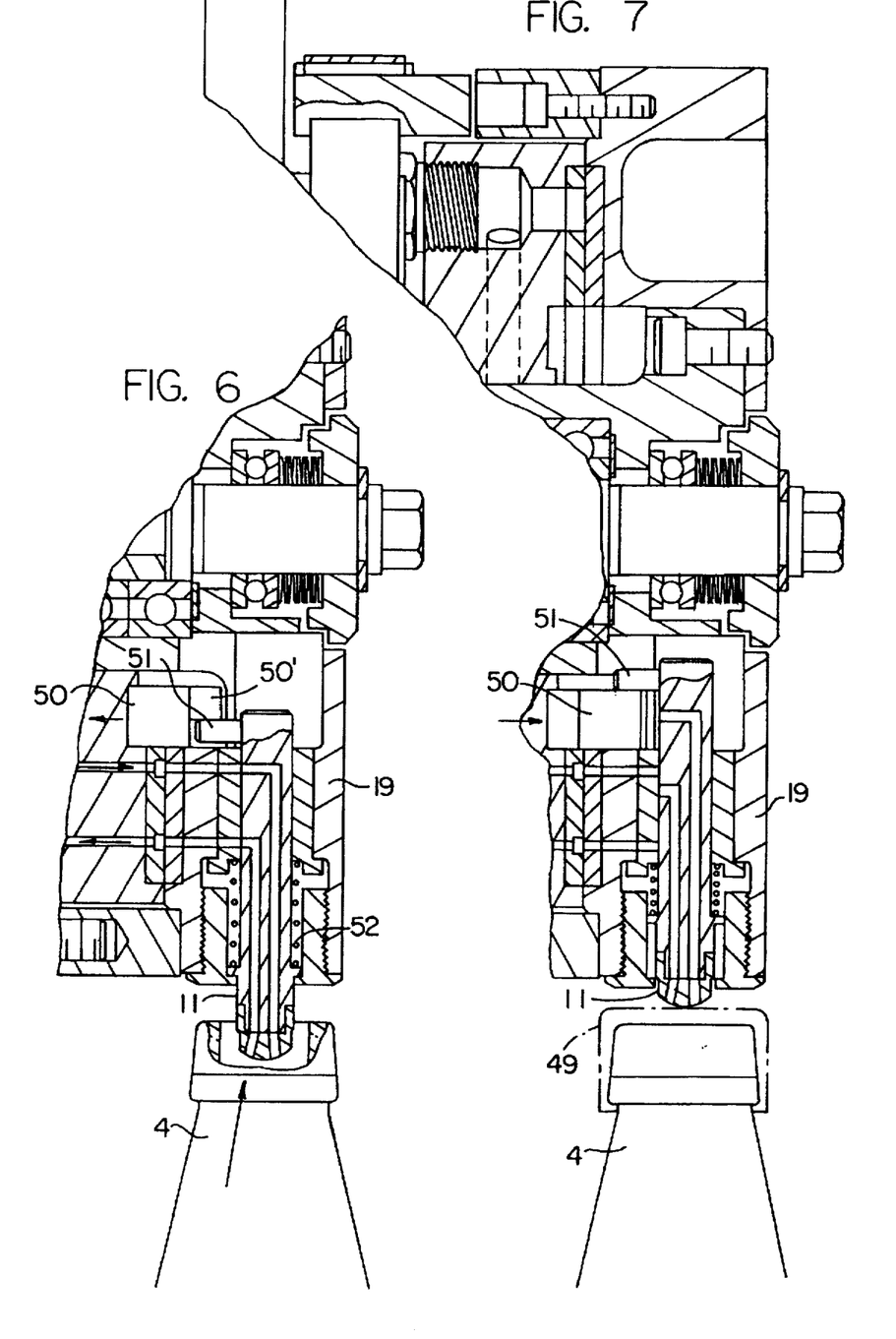
FIG. 6 is a partial vertical section through the sampling head of FIG. 5 in a first position.
FIG. 7 is another partial vertical section through the sampling head of FIG. 5.

FIGS. 5, 6 and 7 show a further embodiment of the invention, in which the head 5 is again equipped with six projecting elements 11 to 16 and the gas samples are fed in basically the same way as in the previous example. In the embodiment shown in FIGS. 5 to 7, however, a special configuration ensures that the elements 11 to 16 do not dip into the container if the container is still capped (cap detector 48) or still contains a large amount of liquid (liquid detector 48') so that liquid could be drawn in by the elements 11 to 16, possibly damaging the analysing instruments.

For this purpose the elements 11 to 16 are radially displaceably mounted in the disk-shaped head 5, and a retracting device is provided allowing each individual element to retract in the region of the container. FIG. 5 shows in unbroken lines a sectioned view of an element 11 in the normal position shortly before the point at which it would dip into the container 4. However, a detector 48 has established that the relevant container 4 still carries a cap 49. A two-piece control ramp 50 and 50', which does not affect the element in the normal position (FIG. 6), now causes the element 11 to be retracted radially towards the centre of the disk so that the element does not contact the cap 49. FIG. 5 shows in unbroken lines a series of positions adopted by the element 11 as a result of this retraction. At the end of what would normally be the withdrawal phase of a sampling procedure, the element 11 is fully extended once again.

As FIG. 6 shows, in its normal position the control ramp 50 is retracted so that a stud 51 attached to the element 11 displaceably mounted in the rotatable part 19 does not normally run onto the ramp. If, as shown in FIG. 7, the control ramp 50 is pushed forwards e.g. by electromechanical, pneumatic or hydraulic means, the stud 51 runs on to the ramp 50, causing the element 11 to retract. At the end of the ramp 50' (whose profile can be seen in FIG. 5, in which various positions of the stud 51 are also shown) the element 11 is returned to its normal position by the spring 52. The control ramp 50 is retracted as soon as the stud 51 has run on to the fixed ramp 50', to allow the next stud to pass clear in the normal position. The remaining elements 12 to 16 are, of course, also constructed in the same way as the element 11, and are retractable. Upon retraction of an element the gas path through it is interrupted, as can be seen from FIG. 7. The corresponding bottle, which is not analysed, is classed as defective by the control unit of the apparatus and is removed from the conveyor path, in the same way as containers identified as contaminated.

Figure 8:
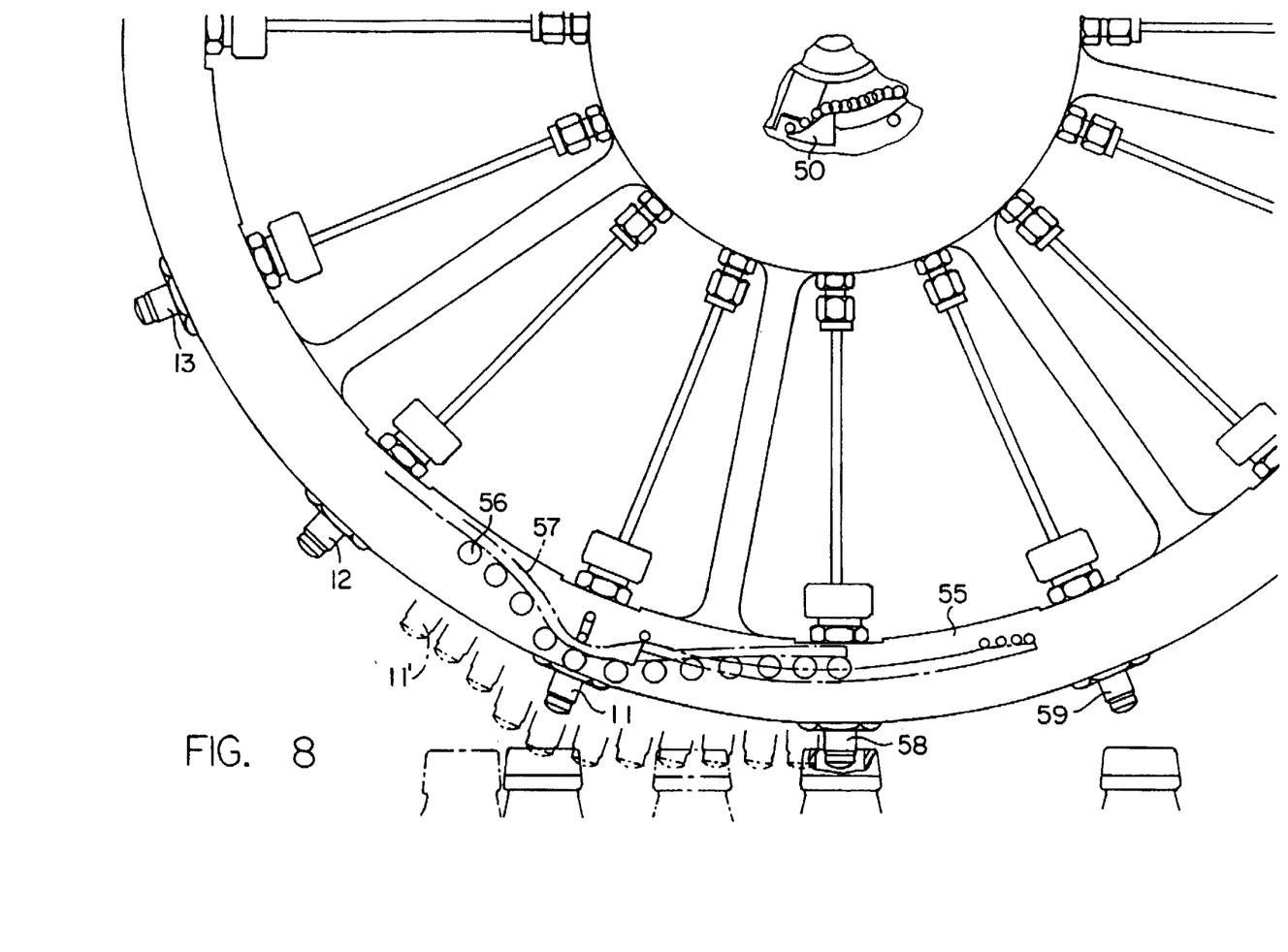
FIG. 8 is a partial view of another sampling head.

FIG. 8 shows part of another embodiment of the sampling head 5. In this embodiment the inner disk of the sampling head, which has basically the same construction as that described in relation to the previous examples, is extended by a ring in the form of a wheel on whose outer circumference sixteen projecting sampling elements, of which only five (11 to 13 and 58,59) can be seen in the figure, are arranged. The inner disk naturally has sixteen corresponding duct arrangements for alternate switching of successive gas samples to the two analysing instruments. The advantage of this design is that the larger outer diameter results in a lengthened co-travel path for each insertion element and its container and a longer dwell time of the insertion element in the container. The disk/ring construction means that the sealing face 22 (cf. FIG. 4) between the fixed part and the moving part need be no larger in diameter than in the previously described examples, as is desirable for manufacturing reasons. A disadvantage of the increased outer diameter is the lengthening of the gas paths due to the linking elements 54 between the individual projecting element 11 to 59 and the disk.

This embodiment can also be provided with retracting means for the elements 11 to 59, as indicated by the control ramp 50.

FIG. 8 also serves to indicate a further modification in which the sampling element is pushed forwards at the point of insertion. For this purpose the sampling element is suitably arranged in a displaceable manner in the ring 55 and is provided with a stud 56 which runs on to a fixed cam guide 57, pushing the element forwards as graphically represented in the figure by sequential positions of one element 11'. This forward push results in smooth insertion and an even longer dwell time of the element inside the container.

An advantage common to all embodiments is that the continuously changing angle between the insertion element and the container means that air injection and suction extraction takes place at a changing angle, so mixing the gas more intensively with the contaminating substances, and improving their extraction.

With the apparatus according to the invention it is also possible to heat the gas paths, as is already known from the carousel types of apparatus. For the embodiments of FIGS. 1 to 7, heating is particularly easy, since the gas paths lie mainly in the fixed part, which facilitates the supply of current for heating (slip-ring current transfer is not required). Moreover the gas path in the said embodiments is extremely short compared with known carousel designs. In the case of the embodiment of FIG. 8, the gas path is still considerably shorter than in carousel types of apparatus. However, current to the heating coils would have to be supplied via slip-rings in order to heat the ducts 54.

Vertical adjustment of the sampling head 5 to adapt it to the height of the containers (e.g. 0.5 l, 1.0 l or 1.5 l bottles) has already been mentioned. If the drive unit is not centrally located, a corresponding tensioning device can be provided for the driving belt or chain so that the height adjustment does not require special alteration to the tension of the belt or chain. From this point of view is the central drive shown in FIG. 4 which does not give any problem.

Figure 9:
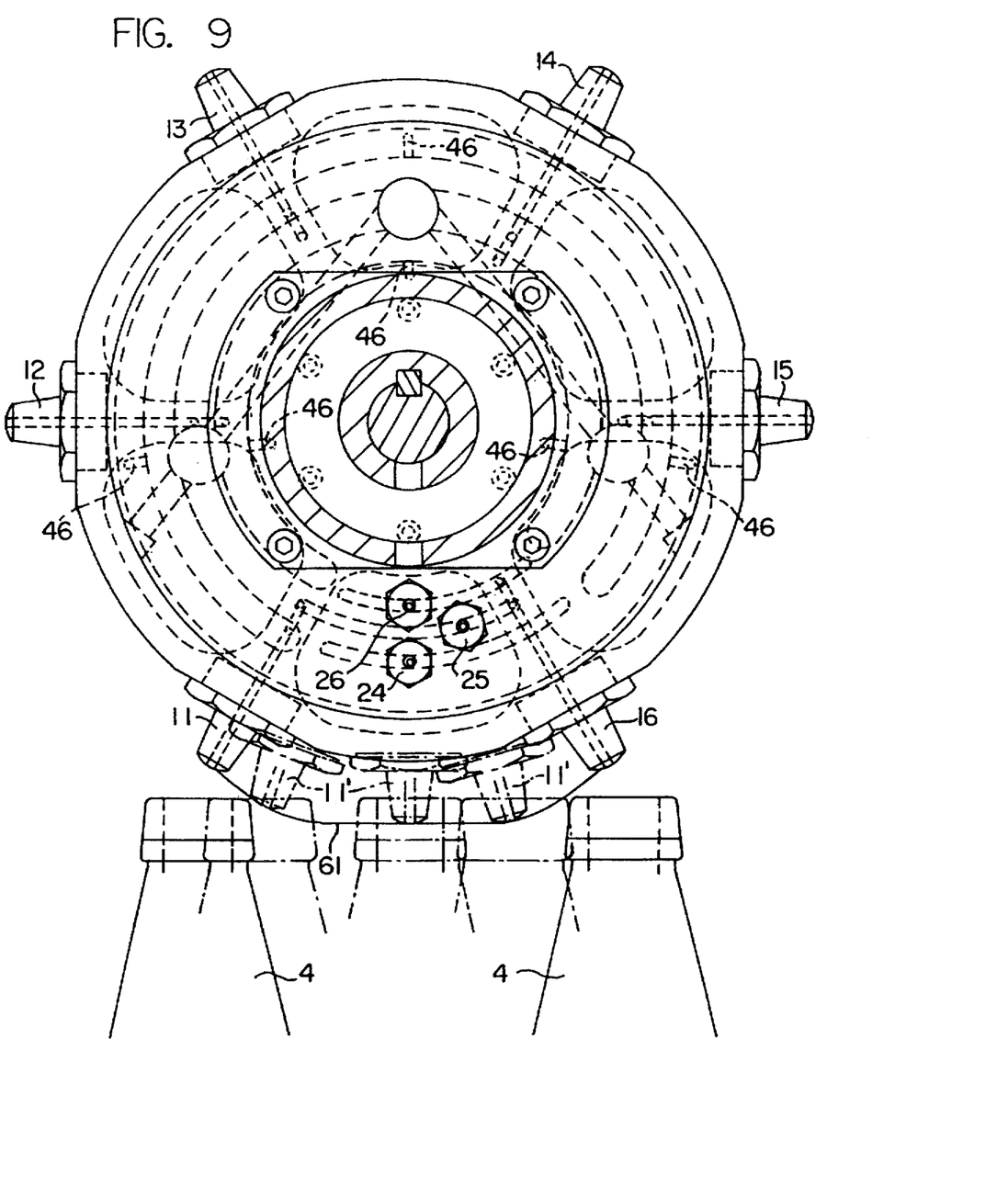
FIG. 9 is a front view of another sampling head.

Alternatively the vertical setting may be performed as a dynamic change of height with a corresponding control unit and high-speed drive (servomotor or stepping motor). In this case, there is no need for individual insertion elements to be retracted owing to the presence of caps or residual liquid, as the entire distributor head or sampling head can be momentarily raised to prevent insertion. The rotational speed is preferably also adjusted to ensure that the container is tracked in a synchronised manner following the change in height. A further variant of the vertical adjustment includes an additional facility for lowering the entire head 5 to increase the depth of insertion and/or to extend the insertion time. Such an effect is depicted in FIG. 9, where the curve 61 illustrates how the lowering of the head affects the insertion of the sampling elements. Also illustrated in FIG. 9 are radial passageways 46 which are in communication with the suction connection 40. These suction passages 46 serve to clean this bearing face between the fixed part 18 and the moving part 19.

In a further embodiment the head 5 is displaceable in the direction of, and in the direction opposite to, the conveyor path, thus affording a further freedom of movement. Corresponding coupler-curve, eccentric and x/y drives are known, and will not be described in detail here.

The apparatus is controlled in a known manner by a microprocessor or computer capable of performing the functions which have been described, by means of suitably controlled drive mechanisms.

The preferred use for the apparatus is in the inspection of used multi-trip bottles; but as described, it may be used for the inspection of other containers.

I claim:

1. Apparatus for inspecting containers for the presence of contamination, comprising:

a conveyor device for transporting containers along a conveyor path, a portion of the conveyor path being a linear conveyor path for transporting the containers to an inspection zone; and at least one disk-shaped sampling head positioned at the inspection zone for removing a sample from each individual container as each container is transported along the linear conveyor path, the sampling head being parallel with the conveyor path and supported for rotation about an axis transverse to the conveyor path and having a plurality of projecting elements arranged around a circumference of the sampling head so that a projecting element is inserted into each container as the sampling head rotates and the container is transported through the inspection zone.

2. Apparatus according to claim 1 wherein the projecting elements are radially displaceable towards the center of the sampling head as the sampling head rotates.

3. Apparatus according to claim 2, further comprising:
a cap sensor for detecting the presence of a cap on the container to be sampled, wherein displacement of the projecting elements is triggered by the cap sensor.

4. Apparatus according to claim 2, further comprising:
a sensor for detecting the presence of foreign substances in the container, wherein the displacement is triggered by the sensor for detecting the presence of foreign substances in the container.

5. Apparatus according to claim 3, further comprising:
a liquid sensor for detecting the presence of residual liquid in the container to be sampled, wherein displacement of the projecting elements is triggered by the liquid sensor.

6. Apparatus according to claim 1 wherein the projecting elements are radially displaceable in the direction away from the center of the sampling head, to extend along a length of insertion from the sampling head and into the container.

7. Apparatus according to claim 1, further comprising:
a control drive for vertically displacing the sampling head.

8. Apparatus according to claim 1, further comprising:
a control drive for displacing the sampling head in a direction parallel to the conveyor path.

9. Apparatus according to claim 1, further comprising:
two analyzing instruments for analyzing samples;
a fixed part for supporting the sampling head for rotation and for distributing the samples removed from successive containers to one or both of the two analyzing instruments.

10. Apparatus according to claim 9, wherein the fixed part has a replaceable distributor element for supplying the samples from the sampling head to a single analyzing instrument.

11. Apparatus according to claim 9, further comprising:
a suction pump;
wherein the fixed part has air intake chambers in communication with the suction pump and also with the sampling head to draw atmospheric air through the projecting elements by way of the air intake chambers during the rotation of the sampling head.

12. Apparatus according to claim 11, wherein a bearing face is defined between the fixed part and moving part of the sampling head and at least one radial passageway is in communication with the suction pump to clean the bearing face.

13. Apparatus according to claim 9, further comprising:
a source of a pressurized medium coupled to the fixed part:
wherein the fixed part has a connection through which the pressurized fluid passes into the sampling head and is discharged from the sampling head.

14. Apparatus according to claim 13, wherein the source of a pressurized medium is a source of compressed air.

15. Apparatus according to claim 1, further comprising:
a device for injecting a medium into the container the device being located upstream of the sampling head.

16. Apparatus according to claim 15, wherein the device for injecting a medium injects compressed air.

17. Apparatus according to claim 1, further comprising:
a rotatably-driven conveyor worm positioned along the conveyor path for positioning the containers relative to the sampling head.

* * * * *